United States Patent [19]
Munford et al.

[11] Patent Number: 5,013,661
[45] Date of Patent: May 7, 1991

[54] LIPOPOLYSACCHARIDE-SPECIFIC ACYLOXYACYL HYDROLASE

[75] Inventors: Robert S. Munford; Catherine L. Hall, both of Dallas, Tex.

[73] Assignee: The Board of Regents, The University of Texas System, Austin, Tex.

[21] Appl. No.: 323,679

[22] Filed: Mar. 15, 1989

Related U.S. Application Data

[63] Continuation-in-part of Ser. No. 53,044, May 22, 1987, abandoned, which is a continuation-in-part of Ser. No. 868,428, May 28, 1986, Pat. No. 4,929,604.

[51] Int. Cl.$^5$ .................... C12N 9/18; A61K 31/715; C12P 19/26
[52] U.S. Cl. .................................... 435/197; 435/84; 514/53; 514/54; 536/53; 424/94.61
[58] Field of Search .................... 435/197, 84; 514/53, 514/54; 536/53; 424/94.61

[56] References Cited

U.S. PATENT DOCUMENTS

| | | | |
|---|---|---|---|
| 4,057,685 | 11/1977 | McIntire | 536/18 |
| 4,148,877 | 4/1979 | Choay et al. | 424/92 |
| 4,185,090 | 1/1980 | McIntire | 424/92 |
| 4,242,270 | 12/1980 | Ayme et al. | 260/412.8 |
| 4,435,386 | 3/1984 | Ribi et al. | 424/177 |
| 4,436,727 | 3/1984 | Ribi | 424/177 |
| 4,436,728 | 3/1984 | Ribi et al. | 424/177 |
| 4,505,899 | 3/1985 | Ribi et al. | 514/8 |
| 4,505,900 | 3/1985 | Ribi et al. | 514/2 |
| 4,663,306 | 5/1987 | Cantrell | 514/2 |
| 4,677,194 | 6/1987 | Hao | 530/350 |
| 4,719,202 | 1/1988 | van Boeckel et al. | 514/61 |

OTHER PUBLICATIONS

Kotani, et al. (1985), Infect. Immun., 49:225–237.
Takada, et al. (1985), Infect. Immun., 48:219–227.
Homma, et al. (1985) J. Biochem., 98:395–406.
Galanos, et al. (1984), Eur. J. Biochem., 140:221–227.
Rosner, et al. (1979), J. Biol. Chem., 254:5926–5933.
Gimber and Rafter (1969), Arch. Biochem. Biophys., 135:14–20.
Munford and Hall (1985), Infect. Immun., 48:464–473.
Freudenberg, et al. (1984), Rev. Inf. Dis., 6:483–487.
Kotani, et al. (1984), Infect. Immun., 485:293–296.
Sutherland (1977), "Surface Carbohydrates of the Prokaryotic Cells", pp. 209–245.

Primary Examiner—Elizabeth C. Weimar
Assistant Examiner—Charles L. Patterson, Jr.
Attorney, Agent, or Firm—Arnold, White & Durkee

[57] ABSTRACT

An acyloxyacyl hydrolase from the human promyelocyte cell line HL-60 has been found to specifically hydrolyze fatty acids from their ester linkages to hydroxy groups of 3-hydroxyfatty acids, the latter being being bound in turn to lipopolysaccharide glycosaminyl residues. The hydrolyzed fatty acids may include dodecanoic acid, tetradecanoic acid and hexadecanoic acid. This enzyme showed a molecular weight by gel exclusion chromatography between about 50,000 Daltons and about 70,000 Daltons, and a molecular weight by polyacrylamide gel electrophoresis with sodium dodecylsulphate, using reduced molecular weight standards, of approximately 54,000 to 60,000 Daltons.

Altered bacterial lipopolysaccharide substantially without fatty acids bound in ester linkage to hydroxy groups of 3-hydroxyfatty acids covalently linked to a glucosaminyl moiety of lipopolysaccharide lipid A are produced. Since the structure of the lipid A moiety is highly conserved, acyloxyacyl hydrolase may act on lipopolysaccharide of many different pathogenic bacteria (for example Salmonella, Escherichia, Hemophilus, and Neisseria).

Such altered bacterial lipopolysaccharide, having toxicity reduced more than immunostimulatory activity, may be therapeutically useful: (1) as vaccines to prevent Gram-negative bacterial diseases by inducing antibodies to lipopolysaccharide O-polysaccharide or R-core antigens, (2) as antidotes to treat or prevent Gram-negative bacterial sepsis ("septic shock"), or (3) as adjuvants to enhance formation of antibodies to other antigens. the acyloxyacyl hydrolase itself may be prophylactically or therapeutically useful to detoxify endogenous lipopolysaccharide in patients with Gram-negative bacterial diseases. The enzyme may also be used to remove toxic lipopolysaccharide from therapeutic injectants.

11 Claims, 4 Drawing Sheets

| Lane | Sample | [NaOH] |
|------|--------|--------|
| 1 | SLPS | [1%] |
| 2 | RcLPS | [65%] |
| 3 | RcLPS | [32%] |
| 4 | RcLPS | [20%] |
| 5 | RcLPS | [1%] |
| 6 | SRLPS | [65%] |
| 7 | SRLPS | [28%] |
| 8 | SRLPS | [15%] |
| 9 | SRLPS | [0.6%] |
| 10 | SLPS | [25%] |
| 11 | SLPS | [1%] |

Fig. 6

LIPOPOLYSACCHARIDE-SPECIFIC ACYLOXYACYL HYDROLASE

The United States Government may have rights in the present invention because the development was partially supported by NIH grant R01 AI18188 from the Department of Health and Human Services.

This application is a continuation-in-part of U.S. patent application Ser. No. 053,044 filed May 22, 1987, now abandoned, which is a continuation-in-part of U.S. patent application Ser. No. 868,428 filed May 28, 1986 now U.S. Pat. No. 4,929,604.

BACKGROUND OF THE INVENTION

The present invention relates to the detoxification of bacterial endotoxin (lipopolysaccharide) by enzymatic modification of its lipid A moiety. The prophylactic and therapeutic use of such detoxified endotoxins is also a subject of the present invention.

Animals mount a complex array of inflammatory responses to tissue invasion by Gram-negative bacteria. Many of these responses appear to be provoked by the lipopolysaccharides (LPS) that are present in the bacterial outer membrane. Much evidence suggests that LPS directly stimulates host cells such as macrophages, neutrophils, and endothelial cells, which then mediate the inflammatory changes. Responses to LPS may be toxic (e.g. hypotension or coagulation disturbances) or beneficial to the infected host (e.g. enhancement of antibody formation, mobilization of phagocytes, acute phase protein synthesis, and others).

Figure 1:
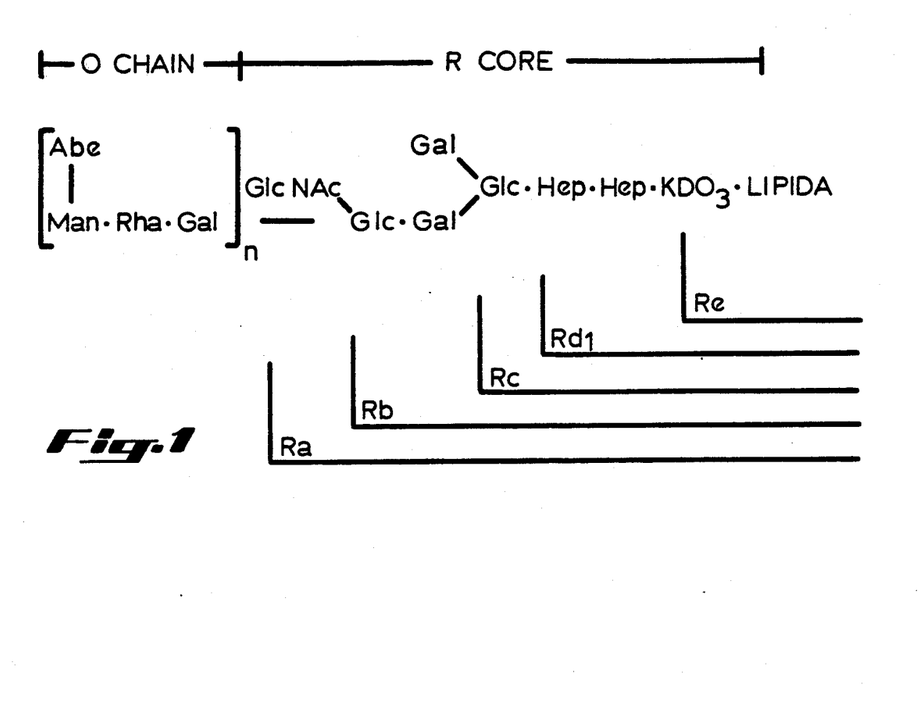
FIG. 1 shows the general structure of Salmonella LPS. LPS is a glycolipid that has a saccharide chain covalently attached to a lipid (lipid A). LPS molecules may have different lengths of saccharide chain. The saccharide chain has two regions, O-antigen and R-core as shown. Molecules that contain both O-antigen and R-core are called "smooth," while molecules that have only R-core are called "rough." S-LPS refers to smooth LPS (i.e., containing O-antigen). R-LPS refers to rough LPS. The R-core is further subdivided, according to its length, from Ra (complete core) to Re (only 2-keto-3-deoxyoctulosonic acid (KDO)). The term "deep-rough" LPS refers to Re LPS. SR-LPS have one O-antigen repeat unit attached to the R-core. n = 0 to more than 50.
Figure 2:
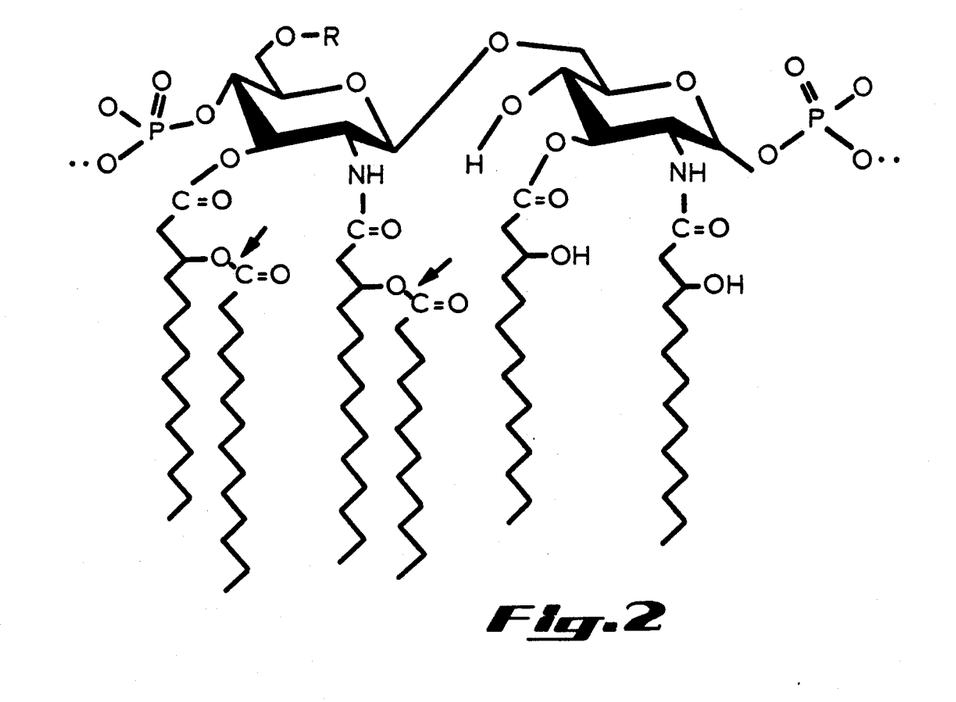
FIG. 2 shows the proposed general structure of enterobacterial lipid A. R = site of attachment of the polysaccharide chain. Arrows indicate the site of action of acyloxyacyl hydrolase.

Typical Gram-negative bacterial lipopolysaccharides (LPS) have 3 major structural regions: the O polysaccharide, the R-core oligosaccharide, and lipid A (FIG. 1 and FIG. 2). The structure of the O polysaccharide is highly variable between organisms, even in the same species, and its antigenicity serves as a basis for serotyping the bacteria. The R region is a bridge between the O-antigen and lipid A; its structure is similar in most Gram-negative bacteria. Antibodies to LPS (typically directed to 0- or R-core antigenic sites) may promote phagocytosis or killing of the bacteria, or they may enhance removal of LPS from the bloodstream into sites (liver, spleen) where the LPS are degraded. The O-antigen, which differs markedly in LPS from different bacterial genera, is the most antigenic component of the LPS. The R region is also highly conserved and is thought to contribute to the stimulatory potency of LPS. The lipid A moiety is remarkably similar in structure across a wide range of bacterial genera.

The lipid A of enteric bacteria (e.g. *Salmonella, E. coli*) is a glucosamine disaccharide that is phosphorylated at positions 1 and 4' and has 6 or 7 covalently-linked fatty acids (FIG. 2). Four molecules of 3-hydroxytetradecanoate (3-OH-14:0) are attached to the glucosamine disaccharide at positions 2, 3, 2', and 3'; the hydroxyl groups of the 3-OH-14:0 residues at positions 2' and 3' (and sometimes 2) are substituted with normal fatty acids (dodecanoate, tetradecanoate, hexadecanoate) to form acyloxyacyl groups. In 1983 the discovery of a novel enzymatic activity was reported. This acyloxyacyl hydrolase activity, found in the granule fraction of human peripheral blood neutrophils, selectively removed some of the nonhydroxylated acyl chains from *Salmonella typhimurium* LPS (Hall and Munford (1983) Proc. Nat. Acad. Sci. V 80, pp 6671-6675). It was known that *Dictyostelium discoideum* (slime mold), which utilizes Gram-negative bacteria as a major foodstuff, contains enzymes that remove nonhydroxylated and hydroxylated acyl chains from LPS (Rosner et al. (1979) J. Biol. Chem. V 254, pp 5926-5933). The experiments of Gimber and Rafter (Arch. Biochem. Biophys, (1969), V 135, pp 14-20) had also suggested that deacylation of LPS is carried out by intact neutrophils. These papers, however, did not show purified enzymes.

Recent studies of the biological activities of chemically synthesized lipid A analogs and biosynthetic precursors of lipid A have provided valuable information about structure-activity relationships (Galanos et al. (1984) Eur. J. Biochem. V 140, p 221; Takada et al. (1985) Infect. & Immun. V 48, p 219; Kotani et al. (1985) Infect. Immun. V 49, p 225; and Homma et al. (1985) J. Biochem. V 98, p 395). Lipid A analogs that lack nonhydroxylated acyl chains are not reactive in the dermal Shwartzman test and have reduced pyrogenicity, yet they are nearly equipotent with complete lipid A in various assays of immune stimulation such as B-cell mitogenicity, adjuvanticity, and stimulation of macrophages to release prostaglandin $E_2$ [$PGE_2$]. However, since the carbohydrate chain that is attached to lipid A in LPS has been shown to have stimulatory potency itself (Lebbar et al., 1986, Eur. J. Immunol. V. 16, 87-91) and to modulate (increase) the potency of lipid A (Galanos, Reitschel, Luderitz, and Westphal, [1972] Eur. J. Biochem. V. 31, 230-233; Kotani et al. [1985] Infection and Immunity V. 49, 225-237), the effects of acyloxyacyl hydrolysis on the biological activities of LPS could not be predicted. The present invention relates to the discovery that acyloxyacyl hydrolysis detoxifies LPS without destroying the immunostimulatory activity.

SUMMARY OF THE INVENTION

An acyloxyacyl hydrolase isolated from human neutrophils has been found to specifically hydrolyze fatty acids from their ester linkages to hydroxy groups of 3-hydroxyfatty acids, the latter being bound in turn through their carboxylate functions to glucosaminyl residues in the lipid A region of LPS. The hydrolyzed fatty acids may include, for example, dodecanoic acid, tetradecanoic acid and hexadecanoic acid. This enzyme, purified from human promyelocytes, has the above described specificity. Gel chromatography of the purified enyzme preparation showed a molecular weight between about 50,000 Daltons and about 70,000 Daltons. Analysis of the enzyme by electrophoresis in 11 % polyacrylamide gels in the presence of sodium dodecyl sulfate showed an apparent molecular weight, using reduced molecular weight markers, of 54,000 to 60,000 Daltons. By the term "purified" as applied to this enzyme, is meant greater than about 90% pure (preferably greater than about 95% pure) as judged by polyacrylamide gel electrophoresis.

Altered bacterial LPS substantially without fatty acids bound in ester linkage to hydroxy groups of 3-hydroxyfatty acids covalently linked to a glucosaminyl moiety of LPS lipid A are produced as described herein. By the term "substantially" as used herein to define the extent of esterified fatty acid removal, is meant greater than about 90% removal of fatty acids normally esterified to the hydroxyl groups of the 3-hydroxyfatty acid moieties. Said altered bacterial LPS characteristically have bound 3-hydroxyfatty acids with hydroxy functions at least substantially unesterified. Since the structure of the lipid A moiety is highly conserved, acyloxyacyl hydrolase may act on LPS of many different pathogenic bacteria (those studied include Salmonella, Escherichia, Hemophilus, and Neisseria).

Such altered bacterial LPS, having toxicity reduced more than immunostimulatory activity, may be therapeutically and/or prophylactically useful. Such therapeutic usefulness comprises use of the altered LPS (1) as vaccines to prevent Gram-negative bacterial diseases by inducing antibodies to 0-polysaccharide or R-core antigens, (2) as antidotes to treat or prevent Gram-negative bacterial sepsis ("septic shock"), or (3) as adjuvants to enhance formation of antibodies to other antigens. The acyloxyacyl hydrolase itself may be therapeutically or prophylactically useful to detoxify endogenous LPS in patients with, or at risk of, Gram-negative bacterial diseases.

BRIEF DESCRIPTION OF THE DRAWINGS

FIG. 4 shows binding of the enzyme to LPS. A preparation of partially purified enzyme was radiolabeled with $^{125}$I. The radiolabeled proteins were then incubated with or without LPS for 1 hour at 22° C. Staphylococci that had been coated with IgG antibodies to the LPS were then added, and after further incubation at 4° C. the staphylococci were washed extensively and then solubilized in SDS digestion buffer (2% SDS, 20% glycerol) and the $^{125}$I-labeled proteins that bound to the staphylococci were analyzed by SDS-polyacrylamide gel electrophoresis and autoradiography. The lane marked * contained the mixture of labeled proteins. Lanes 1 through 4 contained staphylococci that were incubated with the labeled proteins; LPS and anti-LPS antibody were included in the incubation mixtures as indicated. A single radiolabeled protein bound specifically to the staphylococci when both LPS and anti-LPS were included (lane 3). This is the same band that is associated with enzymatic activity in all other purification steps.

DESCRIPTION OF THE PREFERRED EMBODIMENT

The present invention involves the use of a hydrolytic enzyme to detoxify bacterial lipopolysaccharide (LPS or endotoxin). This detoxification involves the hydrolysis of the ester bonds between nonhydroxylated acyl functions and the hydroxy groups of 3-hydroxymyristoyl (3-hydroxytetradecanoate) or other 3-hydroxy fatty acyl residues. These 3-hydroxymyristoyl functions are, in turn, bound in ester or amide linkage to a D-glucosaminyl disaccharide structure of the LPS lipid A moiety (see FIG. 2). The term acyloxyacyl hydrolase is used here to refer to this enzymatic activity.

An acyloxyacyl hydrolase was purified from cells of a human promyelocyte cell line, HL-60, and used to deacylate LPS from S. typhimurium. The enzymatically deacylated LPS lacked nonhydroxylated fatty acids but retained phosphate, 3-hydroxymyristoyl residues, and the polysaccharide chain. The effect of acyloxyacyl hydrolysis on the biological activities of the LPS was studied in several test systems. Loss of bioactivity in these assays was directly related to the degree of deacylation. Removal of approximately 95% of the nonhydroxylated fatty acids from the LPS had relatively minor impact on B-cell mitogenicity (5- to 12-fold loss of activity); intermediate effects on pyrogenicity and Limulus lysate clotting activity, (10- to 20-fold loss of activity); and major impact on preparing the skin for the dermal Shwartzman reaction and on the stimulation of human vascular endothelial cells (greater than 100-fold loss of activity). The tissue toxicity of the LPS, measured in the Shwartzman reaction, was thus reduced at least 10-fold more than the immunosiimulatory activity, measured in the B-cell mitogenicity assay.

Acyloxyacyl hydrolase was released from the granule fraction of dimethylsulfoxide-induced HL-60 cells by detergent solubilization and then purified using a series of chromatographic procedures: blue agarose, phenyl-Sepharose, hydroxylapatite, and cation exchange. From 36 grams of cell lysate protein, approximately 6 micrograms of pure enzyme were obtained.

The discoveries comprising the present invention include the first description of a purified enzyme that modifies the bioactivities of LPS. Acyloxyacyl hydrolase activity has been found in human neutrophils, monocytes, and vascular endothelial cells, and in mouse macrophages; the latter cells also contain mechanisms for removing 3-hydroxymyristate residues from LPS. Antibody-opsonized LPS undergo deacylation by both neutrophils and macrophages, so acyloxyacyl hydrolases should act on the LPS in phagocytosed bacteria as well. In addition to *Salmonella* LPS, the enzyme also deacylates LPS from other bacteria (*E. coli, Hemophilus influenzae, Neisseria meninqitidis,* for example). Acyloxyacyl hydrolases are most likely located in an acid intracellular compartment (lysosomes or endosomes), where deacylation of bacterial LPS would accompany the digestion of other bacterial components. Neutrophils are the front line of host defense against bacterial invasion, yet they are short-lived in tissue and also appear to regurgitate part of the material that they ingest; partially deacylated LPS, released from the neutrophils, may then interact with other host cells. It should be emphasized that the intracellular fate of LPS is not completely understood and that existing studies have all dealt with purified LPS, not the LPS in bacteria per se. Presently unknown deacylases, acyl transferases, or phosphatases may also process LPS intracellularly, with a variety of potential effects on LPS bioactivity.

It should also be noted that the present inventors have found acyloxyacyl hydrolase activity in the serum of rabbits, mice, cows, pigs, chickens and man. Low levels of activity are present in normal mouse and rabbit serum; these levels can be increased 3- to 15-fold by immunization of rabbits with Gram-negative bacteria or by intravenous innoculation with LPS. The rabbit serum acyloxyacyl hydrolase activity has a somewhat higher pH optimum (5 to 6) than that found for human neutrophil acyloxyacyl hydrolase (4.5 to 5.0). Although normal human serum does not appear to have detectable acyloxyacyl hydrolase activity, low levels of activity have been found in the plasma of some patients with Gram-negative bacterial bloodstream infection. These preliminary studies suggest that animals respond to Gram-negative bacterial immunization or infection by increasing the acyloxyacyl hydrolase activity in their blood. Presumably the enzyme(s) in blood may either (1) bind to circulating LPS, targeting the LPS to be taken up by phagocytic cells, where acyloxyacyl hydrolysis would occur, or (2) act on LPS in local tissue sites of infection.

The major role of acyloxyacyl hydrolases in animals may be to prevent LPS tissue toxicity. Remarkably, acyloxyacyl hydrolysis has a much smaller negative impact on the immunostimulatory potency of LPS, at least as measured by assays such as B-cell mitogenicity. Preservation of the immunostimulatory activities of LPS would allow animals to derive benefits such as immune priming during health and the enhancement of antibody formation during infections.

Thus, the acyloxyacyl hydrolase may be administered as a therapeutic agent to patients subject to septic shock, for example, due to infection by Gram-negative bacteria. The administration of therapeutically effective amounts of the human acyloxyacyl hydrolase should decrease the toxicity of the bacterial LPS while not abolishing potentially helpful LPS biogenic effects such as B lymphocyte stimulation. A prophylactic use of this enzyme may be appropriate where septic shock is a distinct possibility. These uses may be by the usual modes of administration such as by injection into veins, arteries, or peritoneum. Whether administered therapeutically or prophylactically, exogenous acyloxyacyl hydrolase would supplement the patient's own capacity to produce the enzyme, increasing enzyme levels in blood and, possibly, in phagocytic cells. A normal 70 kg man produces about $1 \times 10^{11}$ neutrophils per day. Sixty micrograms of enzyme are contained in about $5 \times 10^{11}$ HL-60 cells. Thus, if neutrophils and HL-60 cells produce about the same amounts of enzyme, a 70 kg man should produce 10-20 micrograms of acyloxyacyl hydrolase per day, only some of which is released into the plasma. A likely effective therapeutic dose range of the acyloxyacyl hydrolase would be from 10 to 100 micrograms per day. Pharmaceutically acceptable formulations of the enzyme for administration include solutions thereof in acceptable aqueous isotonic solutions preferably buffered at a physiological pH.

The antigenic structure of the polysaccharide regions of LPS is not altered by acyloxyacyl hydrolysis. Enzymatic detoxification of the lipid A region of LPS without destruction of immunostimulatory activity may thus produce non-toxic LPS vaccines; the adjuvanticity of the detoxified lipid A would help promote the formation of antibodies to the polysaccharide antigen(s). As noted above, such antibodies may protect animals from various Gram-negative bacterial diseases.

LPS that have been detoxified by acyloxyacyl hydrolase may also be used therapeutically to antagonize the toxic effects of LPS present in (or released from) infecting bacteria. Enzymically deacylated LPS inhibits the ability of native LPS to stimulate the expression by human endothelial cells of a neutrophil-adherence factor (Pohlman, Munford, and Harlan, J. Exp. Med., V 165, p 1393, 1987). Deacylated LPS were inhibitory when added as long as 60 min after the native LPS. The adherence of neutrophils to endothelial cells is thought to play a role in the toxic effects of LPS.

A further use of the enzyme may be to reduce the toxicity of therapeutic liquid injectants which may be contaminated with LPS. Adding acyloxyacyl hydrolase to the injectant and allowing the enzyme to enzymatically hydrolyze ester bonds should detoxify LPS contained therein.

A quantity of such injectant, contained in an isotonic aqueous solution, for example, would be treated with purified acyloxyacyl hydrolase. The enzyme should be at a concentration between about 0.001 and 1.0 micrograms per liter of injectant (preferably between 0.001 and 0.010); allowed to catalyze its specific ester hydrolysis to detoxify any LPS present (for example, for from about one hour to a week). The enzyme may be attached to a solid matrix for ready removal upon completion of such hydrolysis. The presence of detergent, which might be afterward removed, may be used to further enhance enzyme activity.

The following examples are presented to illustrate preferred embodiments of aspects of the present invention but are not intended to limit the scope of the invention unless otherwise specifically so stated in the claims appended hereto.

EXAMPLE 1

PURIFICATION OF ACYLOXYACYL HYDROLASE

Cell source

HL-60 cells (American Type Culture Collection, Rockville, MD, (ATCC) strain CCL-240) were propagated in RPMI-1640 medium that contained 8% fetal bovine serum (Hyclone), 10 units/ml penicillin G, and 50 ug/ml streptomycin. Typically, cultures of 16 liters in spinner flasks were harvested after 4-5 days of growth at 37° C. in an atmosphere of 5% $CO_2$. Two or three days before harvest, dimethylsulfoxide (1.25%, vol/vol) was added to the culture to induce the enzyme. The cells were collected by centrifugation (500 $\times$ g, 10 min, 4° C.), washed once with PBS (10 mM sodium phosphate, 0.15 M sodium chloride, pH 7.1), and resuspended in 10 ml relaxation buffer (100 mM KCl, 3 mM NaCl, 3.5 mM MgCl$_2$, and 10 mM HEPES, pH 7.4).

The cells were then disrupted by nitrogen cavitation or by using several strokes in a Dounce homogenizer, followed by centrifugation (478 ×g, 5 min, 4° C.) to pellet nuclei and unbroken cells.

Enzyme preparation

Granules containing the enzyme were sedimented by centrifugation at 20,000 × g for 10 min at 4° C. The supernatant was recentrifuged and the combined pellets were resuspended in 27 ml relaxation buffer. Triton X-100 was added (0.5 % vol/vol) and after the suspension sat for 10 minutes in an ice bath, distilled water was added to bring the volume to 30 ml (Triton X-100 concentration of 0.05%). Phenylmethylsulfonylfluoride (PMSF) and pepstatin were added (5 mM and 1 nM, respectively), and the preparation was centrifuged at 100,000 ∴ g for 60 min at 4° C. The pellet was discarded and glycerol was added (20%, vol/vol) to the supernatant, and the supernatant was frozen at −20° C. With the exception of monoS chromatography, — all subsequent purification steps were performed at room temperature and the enzyme was stored between steps at 4° C.

Blue agarose chromatography.

Disodium ethylenediaminetetraacetic acid (5 mM) was added to the thawed supernatant, which was then passed over a column of Blue Agarose, Type 1000 (Sigma). The column was washed sequentially with running buffer (10 mM 2(N-morpholino) ethane sulfonic acid (MES)) pH 6.6, 0.01% Triton X-100, 20% glycerol, 25 mM NaCl) that contained, in ⅓ column volume, 0, 75 mM, and 150 mM KSCN. Elution of the enzyme began with 150 mM KSCN; the remainder of the enzyme was then eluted from the column with two column volumes of 200 mM KSCN. Fractions that contained enzyme were stored at 4° C.

Hydrophobic interaction chromatography

The Blue Agarose eluate was dialyzed against phenyl-Sepharose column buffer (0.2 M [NH$_4$]$_2$SO$_4$, 4 mM NaH$_2$PO$_4$, 6 mM Na$_2$HPO$_4$, 0.04% sodium azide, 0.01% Triton X-100, pH 6.8) at 4° C. for 3 hours (3 buffer changes), then applied to a column containing 10 to 25 ml Phenyl-Sepharose CL-4B. After application of the sample, the column was washed with column buffer until the O.D.$_{280}$ of the eluate reached a low plateau. A linear gradient was then applied to the column, using column buffer and elution buffer (75% ethylene glycol, 1.5 mM NaH$_2$PO$_4$, 8.5 mM Na$_2$HPO$_4$, 0.04% sodium azide, pH 7.2) in a ratio of one part column buffer to two parts elution buffer. Fractions (3 ml) were collected and monitored for enzyme activity and optical density at 280 nm (O.D.$_{280}$) The enzyme eluted with the first half of the peak of O.D.$_{280}$ absorbance. Appropriate fractions were pooled and stored at −20° C.

Hydroxyapatite (HPT) chromatography

The fractions from the preceding step were diluted 3-fold with HPT buffer (0.02 M sodium phosphate, pH 7.0, 0.04% sodium azide, .0.01% Triton X-100) and applied to a 1.0×4.0 cm column of hydroxyapatite (Biorad HPT). Proteins were eluted with a gradient from 0.02 to 0.4 M sodium phosphate in the same buffer. The peak of enzymatic activity eluted at a phosphate concentration of 0.2 M. Glycerol (30%, vol/vol) was added and the fractions that contained the enzyme were pooled and concentrated using a Centricon-30 centrifugation device (Amicon).

Cation exchange chromatography

The concentrated HPT fractions were diluted 10-fold in MonoS start buffer (0.15 M sodium acetate, pH 4.5, 0.05% Triton X-100, 0.04% sodium azide, 2% taurine, 5% 2-propanol), centrifuged to remove particulates, and applied through a 0.22 micron filter to a MonoS column (Pharmacia). Using the FPLC system (Pharmacia), proteins were eluted from the column using MonoS start buffer with a gradient of 0–1.0 M NaCl. The peak of enzymatic activity eluted at a NaCl concentration of approximately 0.27–0.3 M. Glycerol (28% vol/vol) and 0.3 volumes of sodium phosphate (400 mM) were added to the peak fractions before they were pooled and concentrated as described above.

Figure 3:
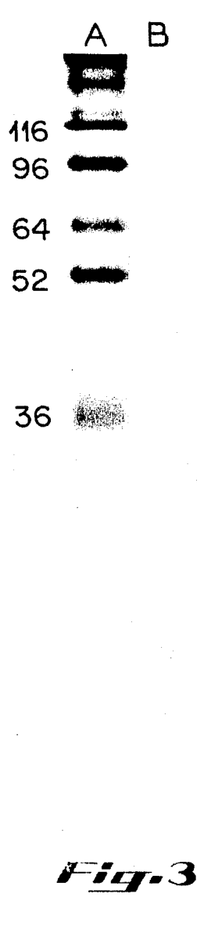
FIG. 3 shows an SDS-polyacrylamide gel (11% polyacrylamide) analysis of purified enzyme. Lane A contains molecular weight markers that had been reduced by exposure to 2-mercaptoethanol and lane B contains purified, unreduced acyloxyacyl hydrolase. The gel was stained with silver. The apparent molecular weight of the unreduced enzyme is 54,000 to 60,000 Daltons.
Figure 4:
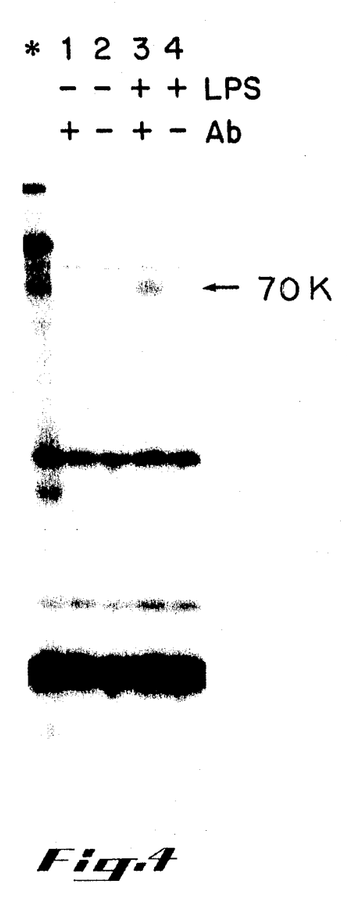

The protein composition of the final preparation was analyzed by polyacrylamide gel electrophoresis using sodium dodecyl sulfate. When stained with silver, the unreduced material showed a single band at an apparent molecular weight of 54,000 to 60,000 Daltons (FIG. 3). After reduction with 2-mercaptoethanol to break disulfide bonds, the major protein band had an apparent molecular weight of 48,000 to 52,000 Daltons. Lower molecular weight (10,000 to 20,000 Daltons) components of the reduced enzyme were detected using 2-dimensional (first dimension, unreduced; second dimension, reduced with 2-mercaptoethanol) electrophoresis of enzyme protein that had been labeled with $^{125}$I. A protein with the same electrophoretic properties and subunit structure as the enzyme was shown to bind to LPS, the substrate for the enzyme (FIG. 4).

A summary of the purification procedure is provided in Table 1.

TABLE 1

PURIFICATION OF ACYLOXYACYL HYDROLASE FROM HL-60 CELLS

| Procedure | Recovery (cumulative %) | | Specific activity |
| --- | --- | --- | --- |
| | Protein | Enzyme activity | Activity/ug protein |
| Post-nuclear lysate | 100 | 100 | 1 |
| Triton X-100 soluble, 100,00 × g supernate of granule fraction | 13.1 | 80.5 | 6 |
| Blue Agarose peak | 0.62 | 62.2 | 98 |
| Phenyl-Sepharose peak | 0.04 | 50.7 | 1,264 |
| Hydroxylapatite peak | 0.0027 | 32.9 | 12,100 |
| monoS peak | 0.000017 | 10.1 | 578,693 |

From 36 grams of post-nuclear lysate, approximately 6.5 micrograms of pure enzyme were obtained.

Alternative cell source

The above methods have also been used to purify acyloxyacyl hydrolase from human peripheral blood neutrophils. The properties of the enzymatic activity obtained from the two sources are essentially identical. Because it may be more readily obtained in larger quantities, the HL-60 cell enzyme has been used for the studies described in examples 2, 3, and 4.

EXAMPLE 2

ACYLOXYACYL HYDROLASE ACTIVITY UPON LPS

Incubation conditions

Biosynthetically radiolabeled LPS were prepared from *Salmonella typhimurium* grown in the presence of $^3$H-acetate and N-acetyl-1-[$^{14}$C]-glucosamine (incorporated into fatty acids and the glucosamine backbone, respectively, of the lipid A region). Acyloxyacyl hydrolysis was followed by measuring the release of $^3$H-fatty acids from the $^{14}$C-glucosamine-labeled LPS backbone.

Double-labeled quantities of ($^3$H/$^{14}$C) LPS (5 ug) were incubated at 37° C. with purified enzyme (10 ul) in a reaction mixture (0.5 ml) that contained 1 mg/ml fatty acid-free bovine serum albumin (BSA) (Sigma), St. Louis Mo), 5 mM CaCl$_2$, 0.5% (vol/vol) Triton X-100, and 20 mM Tris-citrate, pH 4.8. The reaction was stopped at the desired time points by precipitating the LPS and BSA with 1.2 ml 95% ethanol. The precipitate was collected by centrifugation (12,000 × g, 10 min, 4° C.) and washed nnce with 1.0 ml 80% ethanol. The precipitates were suspended in 0.5 ml normal saline and stored at −20° C. Aliquots of the precipitates and supernatants were counted and the percentage of each radiolabel that appeared in the supernatant was calculated. $^{32}$P-labeled *S. typhimurium* Rc LPS, prepared by growing strain PRX20 in a low phosphate medium that contained $^{32}$PO$_4$ (orthophosphate, New England Nuclear, Boston, MA), were incubated in parallel and precipitated in the same way; $^{32}$PO$_4$, when incubated in parallel and processed identically, was completely recovered in the ethanol supernatant.

Fatty Acid Analysis.

LPS were deacylated and precipitated with ethanol, and the ethanol-water supernatant was dried under N$_2$. The $^3$H-fatty acids were extracted into chloroform/methanol (2/1). Unincubated LPS and the deacylated LPS in the ethanol precipitate were hydrolyzed and the liberated fatty acids were extracted into chloroform. Recovery of radioactivity at each step was greater than 85%. The samples were analyzed by one-dimensional TLC using Silica gel G plates (Analtech). The solvent system was petroleum ether/diethyl ether/acetic acid (70/30/1). The spots were scraped from the plate and radioactivity measured (84–96% recovery of added radioactivity). Values reported are the means of duplicate determinations.

Deacylation of LPS.

Figure 5:
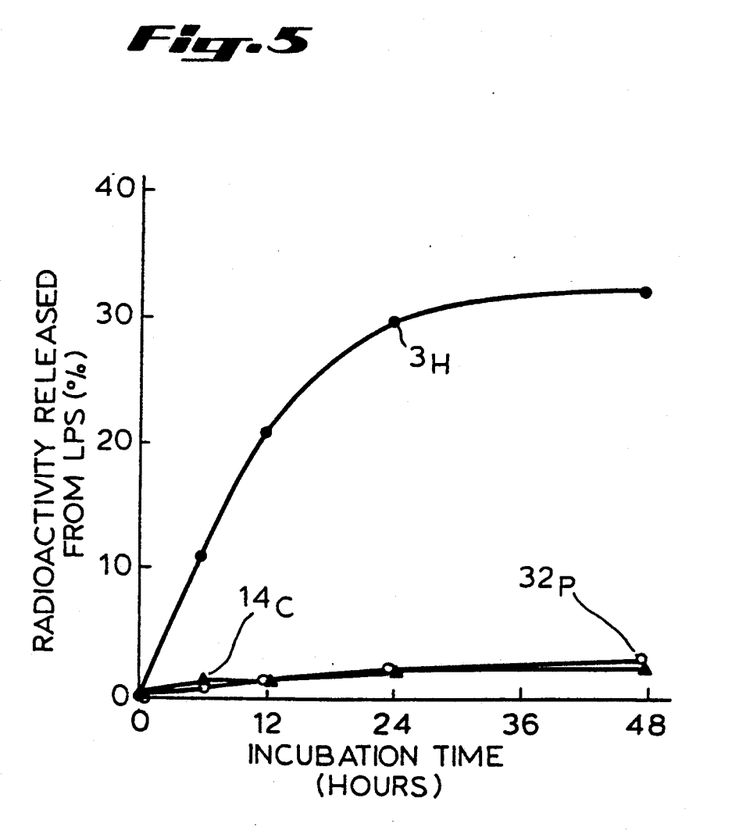
FIG. 5 shows the time course for release of $^3$H-fatty acid, $^{14}$C-glucosamine and $^{32}$P-phosphate from labeled LPS in the presence of acyloxyacyl hydrolase.

The time course of the deacylation reaction is shown in FIG. 5. $^3$H-fatty acids were released from the LPS over time, while neither $^{14}$C nor $^{32}$P (present in $^{32}$P-labeled S. typhimurium LPS that was treated with enzyme in parallel with the $^3$H/$^{14}$C LPS) was released significantly. The reaction reached an apparent maximum when approximately 32% of the $^3$H-fatty acids were extracted from the LPS; since 35% of the $^3$H-counts in this preparation were in nonhydroxylated fatty acids (NFA), 32% deacylation was consistent with nearly complete removal of these residues. This conclusion was supported by analysis of the fatty acid composition of the substrate LPS and the reaction products; 65% of the $^3$H-fatty acid counts in the LPS were in 3-OH-14:0 and 35% were in NFA, whereas the deacylated fatty acids that were released from LPS were almost entirely (94%) nonhydroxylated and 95% of the fatty acids in the partially deacylated LPS were 3-OH-14:0.

Figure 6:
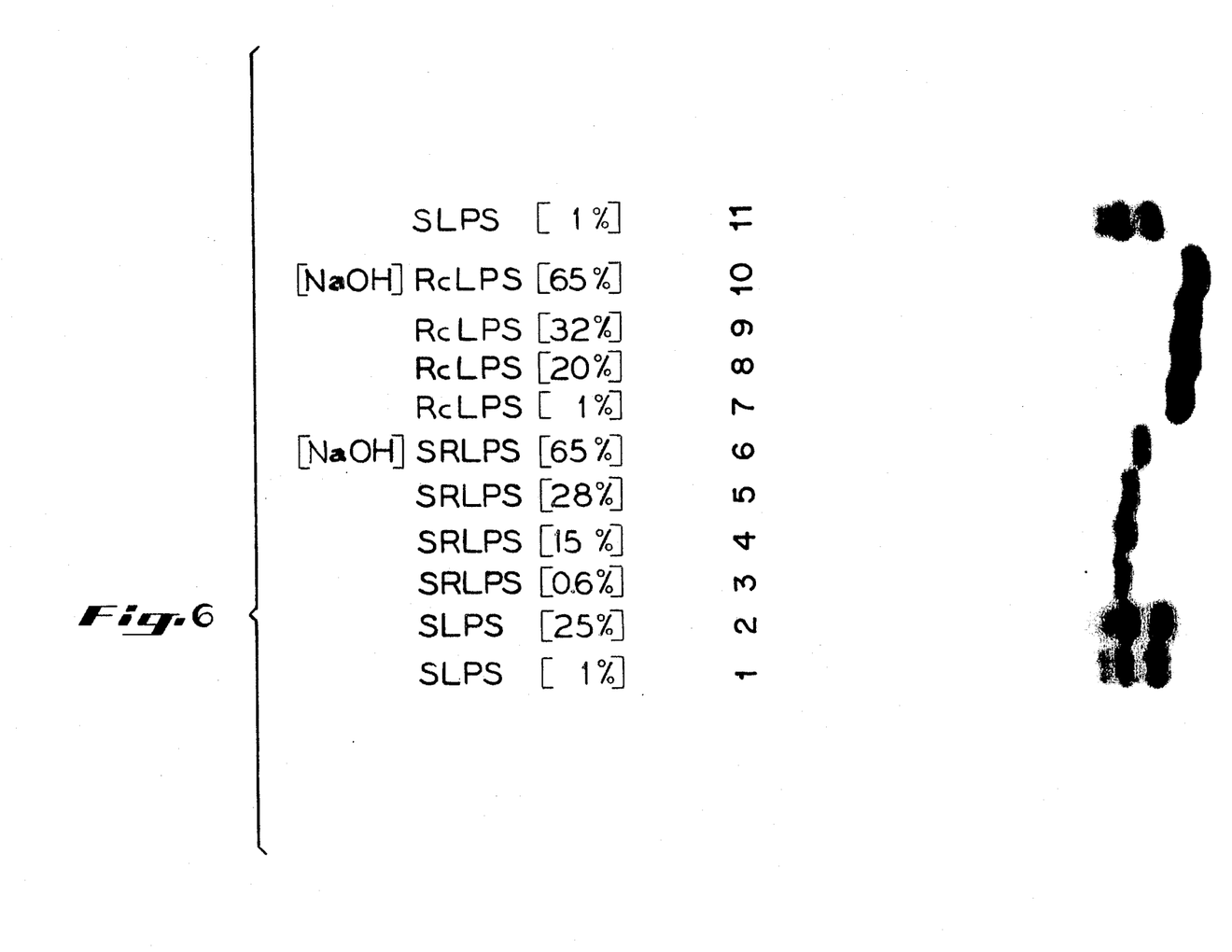
FIG. 6 shows the effects of deacylation upon labeled LPS samples subjected to electrophoresis in polyacrylamide gel with sodium dodecyl sulfate. Each lane contained 0.5 ug LPS. The gel was treated with En$^3$Hance (New England Nuclear) and exposed to Kodak X-Omat XAR-5 film at −70° C. Lane 1 contained S-LPS (about 1% deacylated); lane 2, S-LPS (25% deacylated); lane 3, SRLPS (0.6% deacylated); lane 4, SR-LPS (15% deacylated); lane 5, SR-LPS (28% deacylated); lane 6, SR-LPS (65% deacylated with NaOH); lane 7, Rc-LPS (1% deacylated); lane 8, Rc-LPS (20% deacylated); lane 9, Rc-LPS (32% deacylated); lane 10, Rc-LPS (65% deacylated with NaOH); and lane 11, S-LPS (1% deacylated). The LPS in lanes 6 and 10 were deacylated by treatment with NaOH, which hydolyzed all ester bonds.

As shown in FIG. 6, samples of acylated and deacylated LPS were solubilized in sample buffer and subjected to electrophoresis in polyacrylamide gel with sodium dodecyl sulfate (SDS-PAGE).

Enzymatic deacylation produced an increase in the migration of the LPS in SDS-PAGE, consistent with a reduction in the size of the molecules (FIG. 6). This increase in migration was less than was observed for LPS that had been treated with alkali, which removes all four of the ester-linked fatty acids from lipid A (compare lanes 5 and 6, 9 and 10). Preservation of the original ladder pattern (which reflected the presence of molecules with different numbers of 0-repeat units in the deacylated smooth LPS (lanes 1 and 2) indicated that the polysaccharide chain was not removed by enzymatic treatment.

Taken together, the evidence shows that the only modification in the enzymatically treated molecules was the loss of NFA.

EXAMPLE 3

CHARACTERISTICS OF ACYLOXYACYL HYDROLASE FROM HUMAN NEUTROPHILS

Enzymatic activity was approximately 500,000 fold increased in the MonoS peak fraction relative to the post-nuclear homogenate. The enzymatic activity was abolished by heating for 10 min at 80° C. but was not inhibited by EDTA (10 mM), PMSF (5 mM), pepstatin (1 mM), para-hydroxymercuribenzoate (0.2 mM), sodium fluoride (50 mM), TPCK (0.1 mM), TLCK (0.1 mM), or soybean trypsin inhibitor (10 ug/ml). Calcium chloride (5 -10 mM) and Triton X-100 (0.5 % vol/vol) were required for maximal activity. Sodium deoxycholate (0.1% wt/vol) and 2-mercaptoethanol (100 mM) inhibited the reaction. The enzyme adhered to solid-phase lentil lectin and wheat germ lectin. On gel filtration chromatography, the enzymatic activity eluted as a single peak with an approximate size of 50,000 to 70,000 Daltons. The prior exposure of the preparation to Triton X-100 may artifactually influence this molecular weight estimate. The enzyme also bound to LPS, its substrate. To identify the molecular weight of the LPS-binding material, impure preparations of enzyme that contained approximately 5 protein bands on silver-stained SDS-polyacrylamide electrophoresis gels were radioiodinated and subjected to additional analyses. When the radioiodinated mixture was incubated with LPS, and the LPS was then adsorbed from solution using solid-phase anti-LPS antibodies, a single radioactive protein was found to bind to the LPS. This band had an apparent molecular weight on SDS-PAGE (11% polyacrylamide, using reduced molecular weight markers) of approximately 54,000 to 62,000 Daltons; the same radioactive band co-eluted with enzymatic activity and had an apparent size of 50,000–70,000 on size exclusion chromatography (Superose 12, Pharmacia Labs., Inc., Piscataway, N.J.). When reduced with 2-mercaptoethanol, the LPS-binding protein and the radioiodinated pure enzyme both contained major components at approximately 50,000 Daltons and minor components of approximately 10,000 to 20,000 Daltons.

To test the ability of the purified enzyme to deacylate LPS from different gram-negative bacteria, radiolabeled LPS were prepared from *S. typhimurium* and *E.* coli (2 members of the family *Enterobacteriaceae*), and from 2 distantly related species, *Neisseria meningitidis* (family *Neisseriaceae*) and *Hemophilus influenzae* (family *Brucellaceae*). In each instance, the enzyme preferentially removed the non-hydroxylated fatty acids from the LPS. Since acyloxyacyl linkages have been found in the LPS from all medically important Gram negative bacteria studied, it is likely that susceptibility of LPS to acyloxyacyl hydrolase is a general phenomenon.

The purified enzyme did not contain measurable amounts of phosphatases acting to dephosphorylate either *S. typhimurium* Rc LPS or deep-rough *E. coli* LPS. The absence of such phosphatase activity is preferred for practices of the present invention.

A series of samples that contained increasing amounts of acyloxyacyl hydolase activity was found to have decreasing amounts of hydrolytic activity toward methylumbiliferyl oleate, a substrate for the enzyme, acid lipase. Additionally, it was found that acyloxyacyl hydrolase did not show hydrolytic activity toward cholesterol esters, of toward glycerol trioleate, further distinguishing acyloxyacyl hydrolase from more common hydrolytic enzymes.

EXAMPLE 4

ALTERATION BY ACYLOXYACYL HYDROLASE OF LPS BIOACTIVITIES

R-LPS (rough LPS with short polysaccharide chain) from *S. typhimurium* was treated with acyloxyacyl hydrolase purified as described herein.

The deacylation of LPS was performed by incubating constant amounts of R-LPS and acyloxyacyl hydrolase for different time periods to produce different degrees of deacylation. Background deacylation (LPS incubated without enzyme) of 0.5–2.2% was subtracted from each value. Controls in each bioactivity assay included the reaction mixture and the reaction mixture that contained enzyme but no LPS; these controls were always negative.

The effects of acyloxyacyl hydrolysis on the bioactivities of the LPS were examined in six assays. The dermal Shwartzman reaction and the rabbit pyrogen test were used to measure in vivo toxicity. The mouse spleen cell (B-lymphocyte) mitogenicity assay, the stimulation of murine macrophages to release prostaglandins, and the stimulation of human vascular endothelial cells to express neutrophil-adherence factor were used to measure in vitro bioactivities of LPS.

A dermal Shwartzman reaction was performed by intradermal injection of LPS or enzymically deacylated LPS into New Zealand white rabbits. Twenty-two hours later, the animals were given an intravenous dose of R-LPS (2–4 ug/kg). The dermal lesions were scored 4 to 6 hours later by two persons not knowing the identity of the samples. The average results from two rabbits are presented in the second and third columns of Table 2.

Thermal response index (TRI) for LPS preparations was determined by injecting a New Zealand white rabbit weighing 3–4 kg with an intravenous dose of LPS. Temperature was monitored with a rectal probe and recorded every 10 min. The Thermal Response Index is the integrated product of the temperature above baseline (° C.) and time (degree-hours). (Zimmer et al. (1981) Peptides, V 2, p 413) Each dose was tested in 3 or 4 rabbits.

B-cell proliferation was measured by first incubating LPS preparations with murine splenocytes in 98-well microtiter plates as described by Wannemuehler et al. (1984) J. Immunol. V 133, p 299. After 24 hours, methyl-[$^3$H] thymidine (0.5 uCi) was added to each well. The amount of radioactivity incorporated into each cell culture was measured 18 hours later. Each LPS was tested in four 5-fold dilutions; probit analysis of the results indicated the amount of each preparation that produced half-maximal stimulation of B-cell proliferation. The maximal stimulation index ($^3$H-radioactivity in stimulated cells / $^3$H-radioactivity in unstimulated cells) in the two experiments shown in Table 2 was 30 and 29, respectively.

The fourth assay was the Limulus lysate test, an in vitro clotting assay for LPS. Limulus lysate clotting was measured using 50 ul lysate (Cape Cod Associates, Woods Hole, MA) that contained 0.8 mg/ml n-benzoyl-L-valylglycyl-L-arginine PNA (Vega Biochemicals, Tucson, AZ) and 50 ul test sample. After incubation for 55 min at 37° C., 0.7 ml 40% acetic acid was added to each tube and the absorbance at 405 nm was measured. The values shown were derived b applying the results of 10-fold dilutions of test samples to a standard curve that was constructed with Rc LPS, with normalization to a starting concentration of 10 ug/ml. Dilutions were performed in pyrogen-free water. Each value is the mean of duplicate determinations that differed by less than 10%. Similar results were obtained in two additional experiments.

The stimulation of murine macrophages to relaase prostaglandin $E_2$ was also used as an index of immunostimulatory activity. Thioglycolate-elicited C3H/HeN mouse macrophages were incubated with acylated and 29%-deacylated LPS for 40 hours at 37° C. as described by Munford and Hall (1985) Infection and Immunity, V 48, pp. 464–473. $PGE_2$ levels in the cell supernatants were measured by radioimmunoassay (Campbell et al. (1980) Hypertension, V 2, pp 472–476).

LPS stimulates vascular endothelial cells to express cell-surface factor(s) that promote the adherence of neutrophils to the endothelial cell surface. This activity is thought to play a role in the toxicity of LPS as well as in the attraction of neutrophils to tissue sites of bacterial infection. In collaborative studies, the ability of LPS and deacylated LPS to stimulate the adherence of $^{51}$Cr-labeled human neutrophils to monolayers of human umbilical vein endothelial cells was tested (Pohlman et al. (1987), J. Exp. Med., V 165, p 1393).

The effects of acyloxyacyl hydrolysis on the bioactivities of LPS in these assays were studied in two ways. First, the impact of maximal LPS deacylation (30–32% loss of $^3$H-fatty acids) was assessed in each bioassay. Second, the dose-response relationship (degree of deacylation vs. loss of bioactivity) was studied in three of the assays.

Impact of Maximal Deacylation.

An intradermal injection of LPS, when followed 20 to 24 hours later by an intravenous injection of LPS, produces hemorrhagic necrosis of the skin at the intradermal injection site (dermal Shwartzman reaction). Maximally deacylated LPS (32% loss of $^3$H-fatty acids) did not prepare the skin for the reaction at doses as high as 10 ug, whereas LPS that had been incubated in reaction mixture without enzyme produced hemorrhage (4–5 mm diameter) and induration at doses of 0.1 ug; the reduction in toxicity was thus 100-fold or greater. Deacylated LPS were also substantially less pyrogenic in rabbits than fully acylated LPS. Intravenous doses of 62 ng/kg of acylated and 32%-deacylated LPS produced mean thermal response indices of 12.0±2.5 (S.D.) and 5.0±1.0, respectively, while the indices with 25 ng/kg doses were 8.5±1.9 and 2.8±1.1, respectively. Deacylation of 32% of the $^3$H-fatty acids was associated with approximately 100- to 500- fold loss of stimulatory potency toward human umbilical vein endothelial cells 20-fold loss of activity in the Limulus test, a 5- to 12-fold reduction in B-cell mitogenicity, and a 10- to 20-fold reduction in the release of PGE$_2$ by thioglycolate-elicited murine macrophages. Taken together, these results indicated that maximally deacylated LPS were at least 10-fold less toxic (as measured in the dermal Shwartzman test) than they were immunostimulatory (as measured by the B-cell mitogenicity test).

Dose-response.

Table 2 shows the relationship between the degree of deacylation and the loss of bioactivity for three of the assays. In each assay, loss of activity was directly related to the degree of deacylation.

TABLE 2

EFFECTS OF DEACYLATION ON LPS BIOACTIVITIES

| Deacylation of LPS[1] | Dermal Shwartzman Reaction[2] (0–4+) | | Dose for half-maximal B-cell Proliferation[3] (ug/ml) | | Limulus lysate Activity[4] |
|---|---|---|---|---|---|
| (%) | Rabbit 1 | Rabbit 2 | Expt 1 | Expt 2 | (ug/ml) |
| 0 | 3+ | 3+ | 0.024 | 0.016 | 6.7 |
| 11–15 | 4+ | 2+ | 0.055 | 0.08 | 4.6 |
| 20–22 | 2+ | 2+ | 0.087 | NT | 3.4 |
| 29 | 1+ | 0 | 0.100 | NT | 1.3 |
| 32 | 0 | 0 | 0.14 | 0.18 | 0.4 |

[1]($^3$H-fatty acids released/total $^3$H-fatty acids in LPS) × 100.
[2]Constant amounts (2.5 ug) of R-LPS that had undergone different degrees of deacylation were injected intradermally in New Zealand White rabbits. 0 = no reaction; 1+ = less than or equal to 4 mm hemorrage; 2+ = 5–9 mm hemmorhage; 3+ = 10–15 mm hemorrhage; 4+ = greater than 15 mm hemorrhage.
[3]Single-cell suspensions of C3H/HeN mouse spleen were incubated with LPS in 96-well microtiter plates and incorporation of $^3$H methyl thymidine measured.
[4]Limulus lysate clotting was measured using 50 ul lysate that contained 0.8 mg/ml n-benzoyl-L-valyl-glycyl-L-arginine PNA and 50 ul test sample.

In summary, acyloxyacyl hydrolysis greatly reduced the tissue toxicity of LPS while preserving relatively more of the immunostimulatory activity. This conclusion was consistent with the results of experiments, discussed in Background, that used lipid A analogs to evaluate the stimulatory role of acyloxyacyl groups. Acyloxyacyl hydrolysis makes possible the detoxification of LPS from many different bacteria, including LPS with long polysaccharide chains. The reduction in bioactivity was directly related to the degree of deacylation (Table 1).

Changes may be made in the construction, operation and arrangement of the various elements, steps and procedures described herein without departing from the concept and scope of the invention as defined in the following claims.

What is claimed is:

1. A composition of matter comprising acyloxyacyl hydrolase which is at least 90% pure, said hydrolase being capable of hydrolyzing ester bonds between fatty acids and a hydroxyl function of a 3-hydroxyfatty acid bound to a lipopolysaccharide glycosaminyl residue without hydrolyzing ester or amide bonds between the 3-hydroxyfatty acid and the lipopolysaccharide glucosaminyl residues.

2. The composition of matter of claim 1 wherein the acyloxyacyl hydrolase is obtained from human neutrophils or human promyelocyte cell line HL-60.

3. The composition of matter of claim 1 wherein the acyloxyacyl hydrolase is obtained from human promyelocyte cell line HL-60.

4. The composition of matter of claim 1 wherein the fatty acids are at least one of dodecanoic acid, tetradecanoic acid or hexadecanoic acid.

5. The composition of matter of claim 1 wherein the acyloxyacyl hydrolase is obtained from human neutrophils or the human promyelocyte cell line HL-60 and is capable of hydrolyzing ester bonds between fatty acids or 2-hydroxyfatty acids and a hydroxyl function of a 3-hydroxyfatty acid bound to a lipopolysaccharide glucosaminyl residue.

6. The composition of matter of claim 1 wherein the acyloxyacyl hydrolase has a molecular weight as determined by gel exclusion chromatography of between about 50,000 Daltons and about 70,000 Daltons.

7. The composition of matter of claim 1 wherein the acyloxyacyl hydrolase is essentially devoid of hydrolytic activity toward cholesterol esters, glycerol trioleate, and phosphoryl groups of lipopolysaccharide.

8. The composition of matter of claim 1 wherein the acyloxyacyl hydrolase is obtained from serum or peripheral blood neutrophils.

9. The composition of matter of claim 1 wherein the acyloxyacyl hydrolase has a molecular weight a determined by 11% polyacrylamide gel electrophoresis with sodium dodecylsulfate, using reduced molecular weight standards, of approximately 54,000 to 60,000 Daltons.

10. The composition of matter of claim 9 wherein the acyloxyacyl hydrolase has a binding affinity for lipopolysaccharide.

11. The composition of matter of claim 9 wherein the acyloxyacyl hydrolase is obtained from serum, peripheral blood neutrophils or human promyelocyte cell line HL-60.

* * * * *

UNITED STATES PATENT AND TRADEMARK OFFICE
CERTIFICATE OF CORRECTION

PATENT NO. : 5,013,661

DATED : May 7, 1991

INVENTOR(S) : Robert S. Munford, et al.

It is certified that error appears in the above-identified patent and that said Letters Patent is hereby corrected as shown below:

At column 4, line 50, delete "immunosiimulatory" and insert --immunostimulatory-- therefor.

At column 7, line 21, delete ".·. g" and insert --X g-- therefor.

At column 7, line 36, delete "7/8" and insert --1/3-- therefor.

At column 7, line 58, after '(O.D.$_{280}$)' and before 'The enzyme' insert --.--.

At column 9, line 22, delete "nnce" and insert --once-- therefor.

At column 11, line 21, after 'esters' and before ', glycerol' insert --or toward-- and delete "of toward".

At column 12, line 21, delete "b" and insert --by-- therefor.

UNITED STATES PATENT AND TRADEMARK OFFICE
CERTIFICATE OF CORRECTION

PATENT NO. : 5,013,661

DATED : May 7, 1991

INVENTOR(S) : Robert S. Munford, et al.

It is certified that error appears in the above-identified patent and that said Letters Patent is hereby corrected as shown below:

In claim 9, column 14, line 51, after 'molecular weight' and before 'determined' delete "a" and insert --as-- therefor.

Signed and Sealed this

Twenty-seventh Day of October, 1992

*Attest:*

DOUGLAS B. COMER

*Attesting Officer*     *Acting Commissioner of Patents and Trademarks*